US00PP27494P2

(12) United States Plant Patent
Giesen

(10) Patent No.: US PP27,494 P2
(45) Date of Patent: Dec. 20, 2016

(54) ***LOBELIA* PLANT NAMED 'LOBZ0008'**

(50) Latin Name: ***Lobelia erinus* L.**
Varietal Denomination: LOBZ0008

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,195

(22) Filed: Aug. 14, 2015

(51) Int. Cl.
*A01H 5/02* (2006.01)

(52) U.S. Cl.
USPC ..... Plt./451

(58) Field of Classification Search
USPC ..... Plt./451
See application file for complete search history.

*Primary Examiner* — Susan McCormick Ewoldt
(74) *Attorney, Agent, or Firm* — Joshua L. Price

(57) ABSTRACT

A new *Lobelia* plant named 'LOBZ0008' particularly distinguished by medium large, light blue flowers with narrow white markings, strong stems with medium long inflorescences, dark green foliage, rounded leaves, free branching, and a compact, tight and upright plant habit.

1 Drawing Sheet

Latin name of the genus and species of the plant claimed: *Lobelia erinus* L.

Varietal denomination: 'LOBZ0008'.

BACKGROUND OF THE NEW PLANT

The present invention comprises a new and distinct cultivar of *Lobelia*, botanically known as *Lobelia erinus*, and hereinafter referred to by the cultivar name 'LOBZ0008'.

'LOBZ0008' is a product of a planned breeding program. The new cultivar has medium large, light blue flowers with narrow white markings, strong stems with medium long inflorescences, dark green foliage, rounded leaves, free branching, and a compact, tight and upright plant habit.

'LOBZ0008' originates from a hybridization made in May 2008 in Andijk, The Netherlands.

The female parent was the proprietary (now commercial) *Lobelia* plant 'Tech Heplib', U.S. Plant Pat. No. 20,760, initially designated 'LOB04-286-1', having light blue flowers, upright plant habit with dark leaves and strong, short stems. This variety has smaller flowers and darker green foliage than 'LOBZ0008'.

The male parent of 'LOBZ0008' was the proprietary *Lobelia* plant identified as 'LOB07-204-2' (unpatented), with deeper blue flower color, longer stems, and more trailing plant habit than 'LOBZ0008'.

The resulting seed was sown in June 2009 and 'LOBZ0008' was selected as one flowering plant within the progeny of the stated cross in August 2009 in a controlled environment in Andijk, The Netherlands.

The first act of asexual reproduction of 'LOBZ0008' was accomplished when vegetative cuttings were propagated from the initial selection in January 2010 in a controlled environment in Andijk, The Netherlands.

BRIEF SUMMARY OF THE INVENTION

Horticultural examination of plants grown from cuttings of the plant initiated in the spring of 2011 in Andijk, The Netherlands, and continuing thereafter, has demonstrated that the combination of characteristics as herein disclosed for 'LOBZ0008' are firmly fixed and are retained through successive generations of asexual reproduction.

'LOBZ0008' has not been observed under all possible environmental conditions. The phenotype may vary significantly with variations in environment such as temperature, light intensity, and day length.

A Plant Breeder's Right for this cultivar was applied for with the European Union on Aug. 29, 2014, No. 2014/2116. 'LOBZ0008' has not been made publicly available more than one year prior to the filing of this application.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

The accompanying photographic drawings show typical flower and foliage characteristics of 'LOBZ0008' with colors being as true as possible with an illustration of this type.

Figure 1:
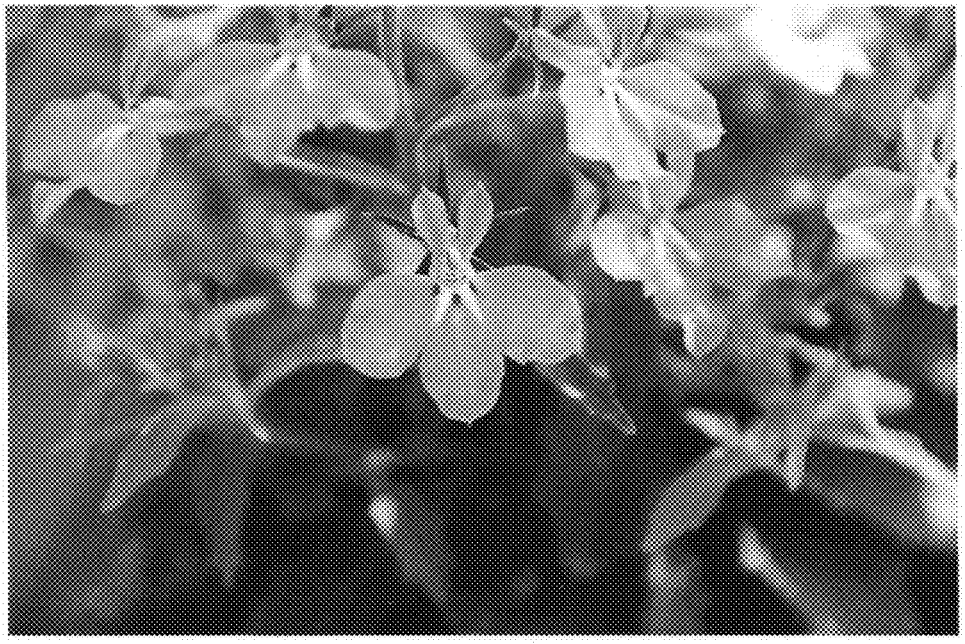
Figure 2:
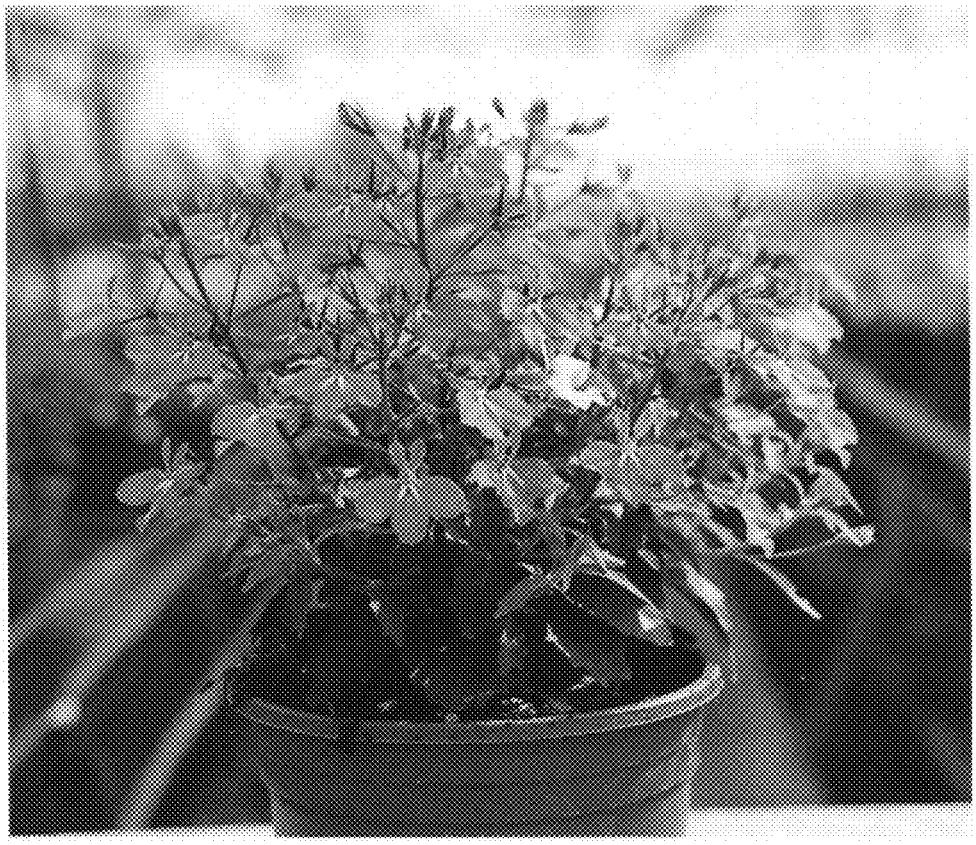

The photographic drawings show in FIG. 1 a close-up of the flowers and in FIG. 2 a flowering potted plant of the new variety.

DETAILED BOTANICAL DESCRIPTION

The aforementioned photographs were taken in late April 2014 from plants grown in a greenhouse trial in Andijk, The Netherlands. The potted plants were growing on benches in a greenhouse and were approximately 12 weeks of age.

The observations and measurements were taken in Andijk, The Netherlands on Aug. 5, 2015 on 12-14 week old plants that were growing outdoors in 25 cm containers. Culture of these plants had started in May 2015 with the planting of rooted cuttings, 1 plant per container, and pinching about two weeks later.

Color references are made to The Royal Horticultural Society Colour Chart (R.H.S.), 2001.

TABLE 1

DIFFERENCES BETWEEN THE NEW VAREITY 'LOBZ0008' AND A MOST SIMILAR VARIETY

| | 'LOBZ0008' | 'LOBZ0004' (U.S. Plant Pat. No. 24,721, commercially known as 'Techno Heat Upright Light Blue') |
|---|---|---|
| Flowering: | More floriferous | Fewer flowers |
| Flower, main color and markings: | Somewhat deeper blue hue, narrow white stripes and 3 tiny deep blue dots | Paler blue hue, larger white zone, no dark dots |
| Plant habit: | More compact, more mounding | More open |

Plant:

*Growth and habit*.—Compact growth habit; dense, and freely branching with short internodes, Upright plant habit.

*Height*.—About 10-12 cm (from top of soil).

*Height* (*inflorescence included*).—About 28 cm.

*Width* (*horiz. diameter*).—From 25-30 cm.

*Branching characteristics*.—7 main stems, each with 3-4 secondary branches.

*Time to produce a finished flowering plant*.—About 11 weeks for a 12 cm pot.

*Garden performance*.—Used as patio planters, in mixed container plantings, or in garden beds.

*Time to initiate and develop roots*.—21-28 days at 20-23° Centigrade.

Roots:

*Number of days to initiate roots*.—About 15 days at about 22 degrees C.

*Number of days to produce a rooted cutting*.—21-25 days.

*Type*.—Fibrous and freely branching.

*Color*.—RHS N155A.

Foliage:

*Arrangement*.—Alternate.

*Leaf shape*.—Oblanceolate.

*Apex*.—Obtuse.

*Base*.—Attenuate.

*Margin*.—Entire to slightly incised.

*Leaf length*.—2.5-4.5 cm.

*Leaf width*.—0.4-0.8 cm.

*Immature leaf, color upper surface*.—RHS 137B.

*Immature leaf, color lower surface*.—RHS 138A.

*Mature color upper surface*.—RHS 147B.

*Mature color lower surface*.—RHS 147C.

*Venation type*.—Pinnate.

*Venation color, upper surface*.—Same color as leaf blade.

*Venation color, lower surface*.—A little protruding, same color as leaf blade.

*Texture*.—Weak pubescence, both surfaces.

*Petiole*.—No petiole, leaves are sessile.

Stem:

*Characteristics*.—With slightly strengthened, protruding edges, side branches are developed at almost every node.

*Stem length*.—8-9 cm.

*Diameter*.—0.2-0.4 cm.

*Internode length*.—2-3.5 cm.

*Color*.—Mainly RHS 145A.

*Texture*.—Finely pubescent.

Inflorescence:

*Type*.—Raceme, composed of single flowers in an alternate arrangement with one flower per node, subtended by a small leaflet.

*Blooming habit*.—Continuously through the growing season from spring to the fall.

*Quantity of inflorescences per plant*.—About 250 per container/50 per plant.

*Quantity of flowers per inflorescence*.—Up to 16 open flowers, and additional buds.

*Lastingness of individual blooms on the plant*.—3-6 days, depending on temperature.

*Fragrance*.—None.

*Inflorescence length*.—18 to 20 cm.

Peduncle:

*Color*.—From RHS 143B to RHS 144B.

*Length*.—7-8 cm.

*Diameter*.—0.2 cm.

*Texture*.—Pubescent.

Pedicels:

*Color*.—RHS 147C.

*Length*.—1.3-1.5 cm.

*Diameter*.—0.1 cm.

*Texture*.—Pubescent.

Flower:

*Corolla type and shape*.—Single, zygomorphic; upper lip is formed by two small petals, lower lip has three larger petals; petals are fused at the base forming a relatively long funnel-shaped tube.

Flower bud:

*Shape*.—Elongate.

*Length*.—0.9 cm.

*Diameter*.—0.4-0.5 cm.

*Color* (*at tight bud*).—RHS 157B (greenish white) and RHS N100C (light blue).

Immature flower:

*Main color upper surface*.—RHS 100C.

*Main color lower surface*.—RHS 101C.

*Immature flower, width*.—1.0 cm.

Mature flower:

*Flower,* (*horizontal*) *length*.—2 cm.

*Flower,* (*horizontal*) *width*.—2 cm.

*Flower, vertical length* (*depth*).—2.1 cm.

*Color upper lip, upper surface*.—RHS 100C.

*Color upper lip, lower surface*.—RHS 101C.

*Upper petal lobes, length* (*from the tube opening*).—1-1.1 cm.

*Upper petal lobes, width*.—0.2-0.3 cm.

*Nectaries at base of lower petals*.—RHS 94B.

*Lower petal lobes, length* (*from the corolla opening*).—1-1.2 cm.

*Lower petal lobes, width*.—0.6-0.9 cm.

*Tube, color* (*outside*).—RHS 94A.

*Tube length*.—0.9-1 cm.

*Tube width*.—0.3-0.4 cm.

Petal (lobes):

*Shape*.—Obovate.

*Apex shape*.—Mucronulate.

*Base*.—Fused, funnel-shape.

*Margin*.—Entire.

*Texture upper surface*.—Glabrous.

*Texture lower surface*.—Short hair, mainly along the mid vein.

Calyx:

*Shape*.—5 sepals in a whorl, slanting outwards, fused at the base.

*Sepal color*.—RHS 187B.

*Sepel length* (*free ends*).—0.7 cm, respective 0.9 cm when including the funnel shaped part.

*Width*.—0.1 cm.

*Shape*.—Ligulate.

*Apex*.—Acute.

*Base*.—Fused.

*Texture*.—Pubescent.

Reproductive organs:

*Stamens*.—Quantity: 5. Filament, color: RHS 92A. Filament length: 0.6 cm. Filament, diameter: 0.1 cm. Anther color: RHS 202A. Anther length: 0.2 cm. Pollen amount: Little. Pollen color: RHS 3B.

*Pistil*.—Quantity per flower: 1. Length: 0.9 cm. Stigma color: RHS 147 B. Stigma length: 0.25 cm. Style color: RHS 145C. Style length: From 0.5-0.7 cm.

Fruit and seed set: Occasionally observed outdoors.

Disease and insect resistance: Resistance and susceptibility typical for the species, no special observations made.

The invention claimed is:

1. A new and distinct cultivar of *Lobelia* plant named 'LOBZ0008' as shown and described herein.

* * * * *